(12) United States Patent
Yasushi et al.

(10) Patent No.: US 7,526,333 B2
(45) Date of Patent: Apr. 28, 2009

(54) SOUND REPRODUCTION SYSTEM AND METHOD BASED ON PHYSICAL AND MENTAL STATES OF A DRIVE

(75) Inventors: Mitsuo Yasushi, Tsurugashima (JP); Masatoshi Yanagidaira, Tsurugashima (JP)

(73) Assignee: Pioneer Corporation, Tokyo-to (JP)

( * ) Notice: Subject to any disclaimer, the term of this patent is extended or adjusted under 35 U.S.C. 154(b) by 781 days.

(21) Appl. No.: 10/649,644

(22) Filed: Aug. 28, 2003

(65) Prior Publication Data
US 2004/0044291 A1    Mar. 4, 2004

(30) Foreign Application Priority Data
Aug. 30, 2002    (JP)    ............... P2002-252643

(51) Int. Cl.
*A61B 5/04*    (2006.01)
*G08B 23/00*    (2006.01)

(52) U.S. Cl. .................. 600/519; 600/500; 600/508; 340/575; 340/576

(58) Field of Classification Search ......... 340/575–576; 600/508–509, 513
See application file for complete search history.

(56) References Cited

U.S. PATENT DOCUMENTS

| | | | | | |
|---|---|---|---|---|---|
| 3,922,665 | A | * | 11/1975 | Curry et al. | 180/272 |
| 4,706,072 | A | * | 11/1987 | Ikeyama | 340/576 |
| 5,813,989 | A | * | 9/1998 | Saitoh et al. | 600/484 |
| 6,353,396 | B1 | * | 3/2002 | Atlas | 340/693.9 |
| 2001/0028309 | A1 | * | 10/2001 | Torch | 340/575 |

FOREIGN PATENT DOCUMENTS

| | | | |
|---|---|---|---|
| EP | 0 713 675 | A2 | 5/1996 |
| EP | 1 123 842 | A2 | 8/2001 |
| JP | 6-290574 | A | 10/1994 |
| JP | 08-140949 | A | 6/1996 |
| JP | 8-196637 | A | 8/1996 |
| JP | 2001-282847 | A | 10/2001 |

OTHER PUBLICATIONS

Japanese Office Action dated Mar. 18, 2008 issued in corresponding Japanese Application No. 2002-252643.

* cited by examiner

*Primary Examiner*—Carl H Layno
*Assistant Examiner*—Eric D Bertram
(74) *Attorney, Agent, or Firm*—Sughrue Mion, PLLC

(57) ABSTRACT

One of the objects of the present invention is to provide an system which can detects degradation in a driving mental state of a driver, that is, sleepiness, fatigue, fret, and so on during driving of a vehicle and notifies the driver of the degradation to encourage safe driving and can reproduce sound such as music matching the taste of the user such as a driver while maintaining awakening of the driver of a mobile unit.

The reproduction controlling system for a mobile unit, is provided with a system controlling reproducing device for reproducing a piece of sound data stored in a database during traveling of the mobile unit, a driving information acquiring device for acquiring driving information indicating a driving state of the mobile unit, the driving information including at least heartbeat variation information, an audio component information acquiring device for analyzing an audio component included in the sound data and acquiring audio component information, a judging device for judging mental and physical states of the driver based on the acquired driving information, a selecting device for selecting the sound data to be reproduced; and a control device for controlling the reproducing device to reproduce the selected sound data.

12 Claims, 7 Drawing Sheets

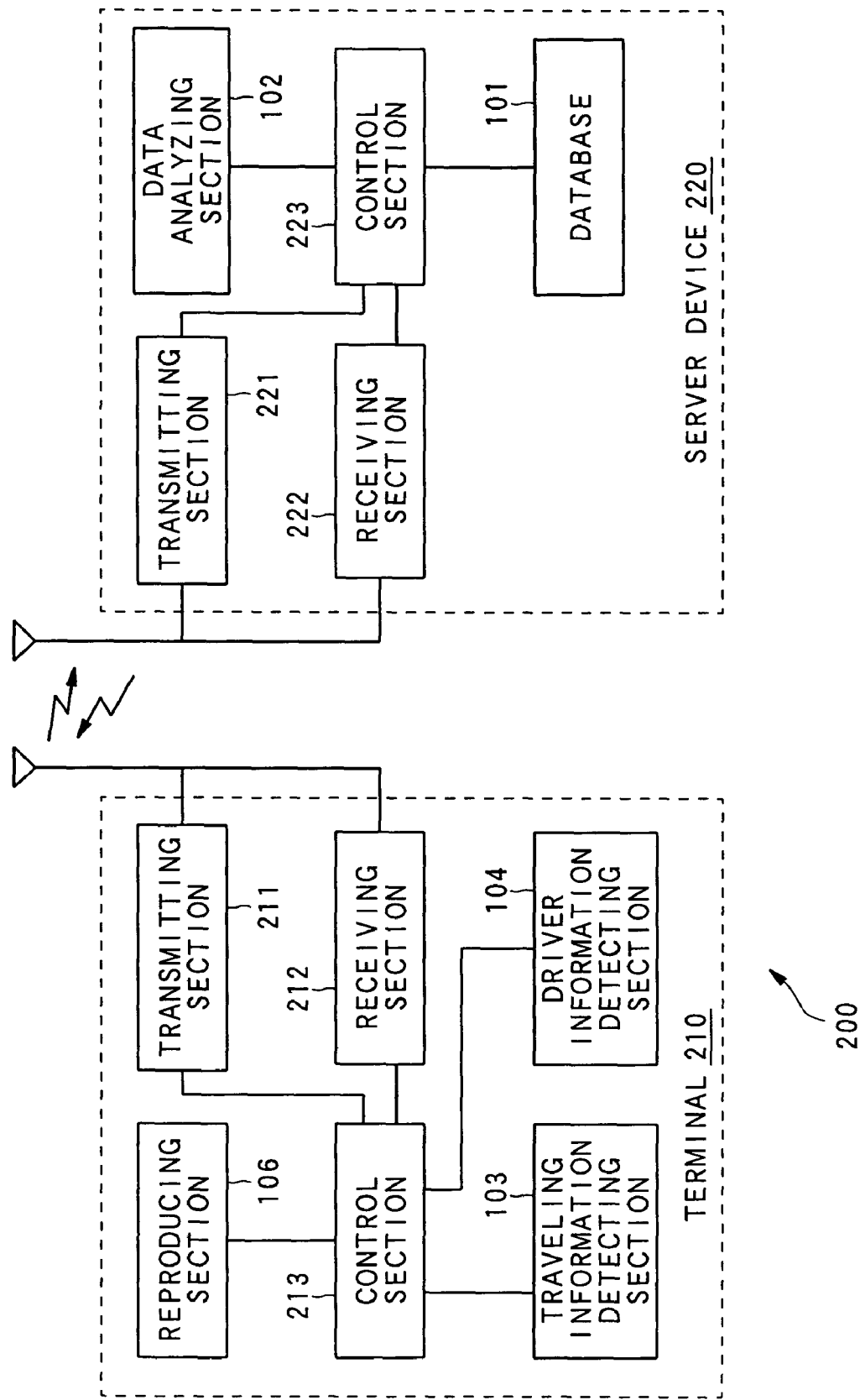

SOUND REPRODUCTION SYSTEM AND METHOD BASED ON PHYSICAL AND MENTAL STATES OF A DRIVE

BACKGROUND OF THE INVENTION

1. Field of the Invention

The present invention relates to a technical field of a reproduction controller for reproducing sound such as music when a mobile unit such as an automobile is driven.

2. Description of the Related Art

In recent years, a driving state detector has been developed which detects degradation in a driving mental state of a driver, that is, sleepiness, fatigue, fret, and so on during driving of a vehicle and notifies the driver of the degradation to encourage safe driving.

Meanwhile, kinds of methods have been studied to prevent an operator from dozing off in a long tedious operation. Recently, devices have been developed mainly for removing a cause of sleepiness, that is, environments suitable for a long tedious operation.

As a representative awakening holding device for preventing dozing by providing such agreeable and comfortable working environments, an awakening holding device described in Japanese Patent Laid-Open No. 8-196637 has been known which reproduces sound at fixed intervals or random intervals according to a circadian rhythm.

The circadian rhythm is considered to appear in an awakening reducing state where balance is lost between an accelerator system for activating brain stem reticular formation from sensory nerves or hypothalamus (autonomic nervous system) and increasing an awakening degree of cerebral cortex and a brake system for reducing an awakening degree by nuclei raphes. In order to hold awakening, it is desirable to change the balancing state into a state where the accelerator system has dominates to control a circadian rhythm phenomenon.

The awakening holding device of the above gazette has a sound source which generates sound for stimulating senses of a person and a measuring section for measuring a circadian rhythm, and the awakening holding device controls reproduction of the sound source so as to change the characteristics of a sound at fixed intervals or random intervals according to a measured circadian rhythm. For example, sound is intermittently reproduced according to the circadian rhythm by installing the awakening holding device in a mobile unit such as a vehicle, and dozing driving can be prevented by stimulating senses of a person.

However, with the above awakening holding device, it is not possible to listen to music selected by the user or music attracting interest of the user.

Particularly, since predetermined music of a reproduced sound source is processed, listening to the sound becomes boring.

SUMMARY OF THE INVENTION

The present invention is devised in view of the above inconveniences. As an example of the solution, a reproduction controller is provided which can reproduce sound such as music matching the taste of the user such as a driver while maintaining awakening of the driver of a mobile unit.

The above object of the present invention can be achieved by a reproduction controlling system of the present invention. The reproduction controlling system for a mobile unit, is provided with a system controlling reproducing device for reproducing a piece of sound data from a plurality of pieces of sound data stored in a database during traveling of the mobile unit, a driving information acquiring device for acquiring driving information indicating a driving state of the mobile unit, the driving information including at least heartbeat variation information indicating a variation in heartbeat of a driver who drives the mobile unit, an audio component information acquiring device for analyzing an audio component included in the sound data and acquiring audio component information indicating the audio component of the analyzed sound data, a judging device for judging mental and physical states of a driver based on the acquired driving information, a selecting device for selecting the sound data to be reproduced based on the acquired audio component information relative to the judged mental and physical states of the driver; and a control device for controlling the reproducing device to reproduce the selected sound data.

According to the present invention, in the case where instructions are provided to reproduce music data, for example, even when the driver is in the mental and physical states of sleepiness, tension, and fatigue, it is possible to stop or suspend the reproduction of music brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

In one aspect of the present invention can be achieved by the reproduction controlling system of the present invention. The reproduction controlling system for the mobile unit of the present invention is wherein when the reproducing device starts reproduction of the sound data or is performing reproduction of the sound data, in the case where the judging device judges that the driver is in the predetermined mental and physical states, the selecting device is provided with a discriminating device for discriminating whether or not the audio component of reproduced data has a component that brings in or enhances the judged mental and physical states based on the audio component information relative to the judged mental and physical states, regarding the reproduced data indicating sound data to be reproduced or sound data being reproduced, a data selecting device for selecting sound data different from the reproduced data as sound data to be reproduced by the reproducing device when the discriminating device judges that the audio component of the reproduced data has a component that brings in or enhances the mental and physical states, and the control device controls the reproducing device to reproduce the selected sound data.

According to the present invention, in the case where instructions are provided to reproduce music data, for example, even when the driver is in mental and physical states of sleepiness, tension, and fatigue, it is possible to stop or suspend the reproduction of the music that brings in or enhances the mental and physical states and to reproduce music data which is different from the stopped or suspended music data and is indicated by the user such as a driver. Hence, it is possible to reproduce music matching the taste of the user while maintaining awakening of the driver of the mobile unit.

In another aspect of the present invention can be achieved by the reproduction controlling system of the present invention. The reproduction controlling system for the mobile unit of the present invention is wherein the judging device judges at least one of the mental and physical states of fatigue, sleepiness, and tension of the driver based on the driving information acquired by the driving information acquiring device.

According to the present invention, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

In further aspect of the present invention can be achieved by the reproduction controlling system of the present invention. The reproduction controlling system for the mobile unit of the present invention is wherein the driving information acquiring device acquires traveling information as the driving information together with the heartbeat variation information, the traveling information indicating a traveling state of the mobile unit.

According to the present invention, since the mental and physical states of the driver can be judged in view of the traveling state, the mental and physical states of the driver can be judged in an appropriate manner.

In further aspect of the present invention can be achieved by the reproduction controlling system of the present invention. The reproduction controlling system for the mobile unit is, wherein the driving information acquiring device acquires at least one of a speed of the mobile unit, a kind of a traveling road where the mobile unit travels, and a turning angle indicating a direction of the mobile unit relative to a traveling direction of the mobile unit, as mobile unit information.

According to the present invention, since the mental and physical states of the driver can be judged in view of the traveling state, the mental and physical states of the driver can be judged in an appropriate manner.

In further aspect of the present invention can be achieved by the reproduction controlling system of the present invention. The reproduction controlling system for the mobile unit of the present invention is, wherein the driving information acquiring device acquires at least one of heart rate data indicating data of a heart rate of the driver and heartbeat fluctuation data indicating data of a fluctuation in heartbeat, as the heartbeat variation information.

According to the present invention, since the mental and physical states of the driver can be judged in view of the traveling state, the mental and physical states of the driver can be judged in an appropriate manner.

In further aspect of the present invention can be achieved by the reproduction controlling system of the present invention. The reproduction controlling system for the mobile unit of the present invention is, wherein the audio component information acquiring device analyzes at least one of sound components of a rhythm pattern, a tempo, a beat, sound image localization, a sound pressure level, and a fundamental note of the sound as sound component information of the sound data, and acquires the analyzed sound component.

According to the present invention, since the mental and physical states of the driver can be judged in view of the traveling state, the mental and physical states of the driver can be judged in an appropriate manner.

The above object of the present invention can be achieved by a reproduction controlling method of the present invention. The reproduction controlling method for a mobile unit is provided with a controlling reproducing process of reproducing a piece of sound data from a plurality of pieces of sound data stored in a database during traveling of the mobile unit, a driver information acquiring process of acquiring driving information indicating a driving state of the mobile unit, the driving information including at least heartbeat variation information indicating a variation in heartbeat of a driver who drives the mobile unit, an audio component information acquiring process of analyzing an audio component included in the sound data and acquiring audio component information indicating the audio component of the analyzed sound data, a judging process of judging mental and physical states of the driver based on the acquired driving information, a selecting process of selecting the sound data to be reproduced based on the acquired audio component information relative to the judged mental and physical states of the driver, and a controlling process of controlling the reproducing device to reproduce the selected sound data.

According to the present invention, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

The above object of the present invention can be achieved by a reproduction controlling computer data signal embodied in a carrier wave of the present invention. The reproduction controlling computer data signal embodied in a carrier wave for a mobile unit, the computer data signal causing a computer to control reproducing device for reproducing a piece of sound data from a plurality of pieces of sound data stored in a database, is caused to serve as an driving information acquiring device for acquiring driving information indicating a driving state of the mobile unit, the driving information including at least heartbeat variation information indicating a variation in heartbeat of a driver who drives the mobile unit, an audio component information acquiring device which analyzes an audio component included in the sound data and acquires audio component information indicating the audio component of the analyzed sound data, a judging device for judging mental and physical states of the driver based on the acquired driving information, a selecting device for selecting the sound data to be reproduced based on the acquired audio component information relative to the judged mental and physical states of the driver; and a control device for controlling the reproducing device to reproduce the selected sound data.

According to the present invention, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

The above object of the present invention can be achieved by a recording medium reproduction controlling computer data signal embodied in a carrier wave of the present invention. The recording medium, wherein a reproduction controlling computer data signal embodied in a carrier wave for a mobile unit of the present invention is recorded so as to be read by a computer.

According to the present invention, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

BRIEF DESCRIPTION OF THE DRAWINGS

FIG. 7 is a diagram showing the configuration of a reproduction controlling system according to Embodiment 3 of the present application.

DETAILED DESCRIPTION OF THE PREFERRED EMBODIMENTS

Referring to the accompanying drawings, the following will describe the embodiments of a reproduction controller which is mounted in a mobile unit such as a vehicle and is used for the mobile unit at the reproduction of music data and the like stored in a CD or a hard disk.

[Embodiment 1]

FIGS. 1 to 6 show Embodiment 1 of a reproduction controller according to the present application. First, referring to FIG. 1, the configuration of the reproduction controller will be discussed in accordance with the present embodiment.

Figure 1:
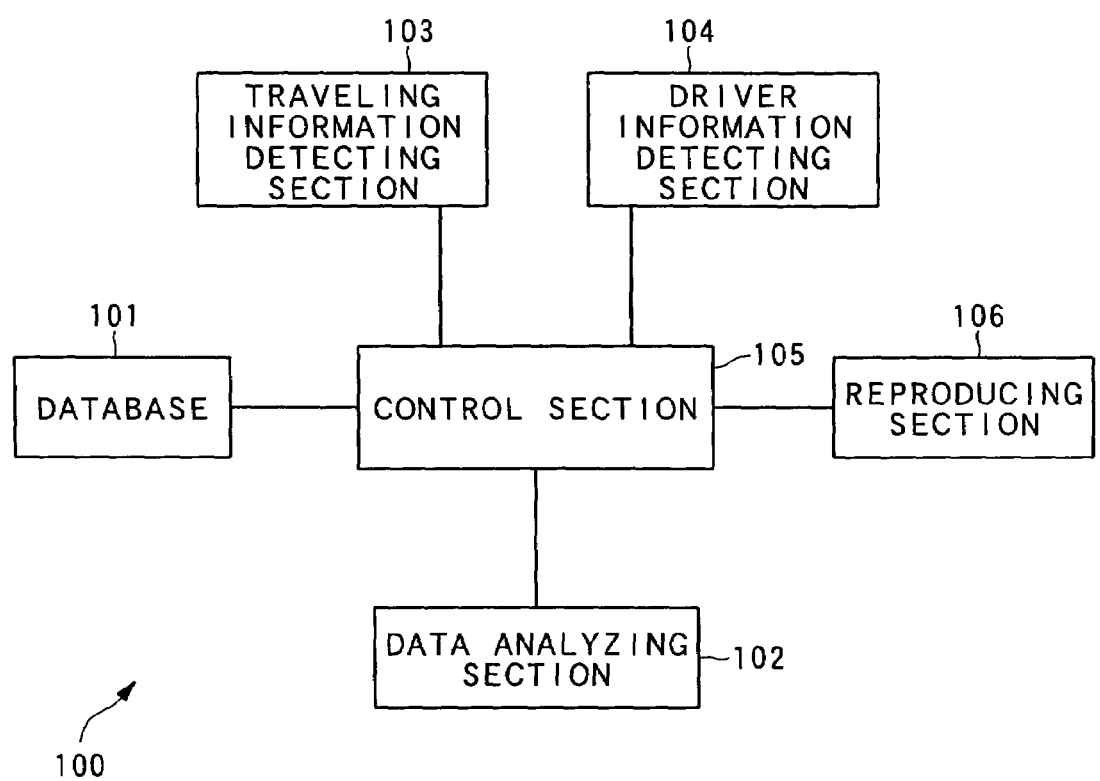
FIG. 1 is a diagram showing the configuration of a reproduction controller according to Embodiment 1 of the present application.

FIG. 1 is a diagram showing the configuration of the reproduction controller according to the present embodiment. The present embodiment will be described on the assumption that the reproduction controller is mounted in a vehicle.

As shown in FIG. 1, a reproduction controller 100 of the present embodiment comprises a database 101 for storing music data in advance, a data analyzing section 102 for performing data analysis on music data, a traveling state detecting section 103 for detecting a traveling state of a vehicle, a driver information detecting section 104 for detecting a driving state of a driver who drives the vehicle, a control section 105 which controls selection of music data reproduced based on the analyzed data (hereinafter, referred to as analysis data) of the analyzed music data, the detected traveling state of the vehicle, and the detected state of the driver, and which controls each of the sections, and a reproducing section 106 for reproducing the music data whose selection has been controlled by the control section 105.

For example, the database 101 of the present embodiment constitutes a database 101 of the present invention, and the data analyzing section 102 of the present embodiment constitutes audio component information acquiring device of the present invention. Moreover, for example, the traveling state detecting section 103 of the present embodiment constitutes driving information acquiring device of the present invention, and the driver information detecting section 104 of the present embodiment constitutes driver information acquiring device of the present invention. Furthermore, for example, the control section 105 of the present embodiment constitutes judging device, deciding device, selecting device, and control device of the present invention, and the reproducing section 106 of the present embodiment constitutes reproducing device of the present invention.

The database 101 is constituted by, for example, a hard disk and stores one thousand or more pieces of music data. As will be discussed later, a piece of music data is outputted to the data analyzing section 102 or the data reproducing section 106 via the control section 105.

When arbitrary music data is selected by the control section 105, the selected music data is inputted to the data analyzing section 102. The data analyzing section 102 performs data analysis on the inputted music data, acquires analysis data of the music data (e.g., corresponding to audio component information of the present invention), and outputs the acquired analysis data to the control section 105.

To be specific, the data analyzing section 102 analyzes music components including a difference in sound pressure between the outputs of right and left speakers, sound image localization such as the perspective of an acoustic image, a tempo indicating the speed of a rhythm in music data, a beat determined by the number and kinds of basic notes in a bar, and a rhythm pattern indicating a pattern of a percussion instrument, and the data analyzing section 102 detects music components concerning a specific chord, which serves as a base for forming the category and atmosphere of music data, as music component information (e.g., corresponding to music component information of the present invention).

For example, when a sound pressure of the output from the speaker is calculated, the data analyzing section 102 calculates acoustic power data for each frequency band of music data and calculates the sum of the acoustic power data for each frequency band to obtain a total acoustic power. A difference in output of the right and left speakers is calculated based on the calculated total acoustic power.

When the perspective of an acoustic image in music data is calculated, the data analyzing section 102 calculates a cross-correlation between the front output and the rear output of the speaker, so that delay time between the front output and the rear output in the music data is obtained. When the delay time is long, the data analyzing section 102 judges that an acoustic image is far away. When the delay time is short, the data analyzing section 102 judges that an acoustic image is close.

Furthermore, in the data analyzing section 102, the acoustic power data of inputted music data is obtained, and an autocorrelation function is calculated relative to a differential value of the acoustic power data, so that a tempo and a beat are calculated. Playing times of several kinds of percussion instruments that are included in inputted music data are calculated, the playing of the percussion instruments is expressed as notes based on the playing times of the percussion instruments, and comparison is made with a rhythm pattern having been stored in an internal memory, so that a rhythm pattern is judged.

Moreover, in the data analyzing section 102, a fundamental note is detected as a base of a chord based on the beat calculated by the above method and a tension code for the fundamental note is calculated, so that the specific chord is detected.

Regarding the detail of the method of detecting a tempo, a beat, a rhythm pattern, and a specific chord in the data analyzing section 102, refer to Japanese Patent Laid-Open No. 6-290574.

The traveling state detecting section 103 detects vehicle information of a vehicle that includes a speed of the vehicle, a traveling direction, and so on. The traveling state detecting section 103 judges a traveling state of the vehicle based on the detected vehicle information and outputs the judgment result as traveling information (e.g., corresponding to mobile unit information and driving information of the present invention) to the control section 105.

For example, the traveling state detecting section 103 has a vehicle speed pulse detecting section which detects a vehicle speed pulse for detecting a speed of a vehicle, and a steering wheel sensor for detecting a turning angle of a steering wheel when a vehicle is driven. The traveling state detecting section 103 judges a traveling road, for example, whether the vehicle travels on an ordinary road or an expressway and whether a traveling place is an urban district or a suburban road, and judges a traveling state of the vehicle, for example, whether the vehicle travels at high speed or in a traffic jam based on information about a speed of the vehicle (hereinafter, referred to as speed information) and information about a turning angle of the steering wheel (hereinafter, referred to as turning angle information). Further, the traveling state detecting section 103 outputs traveling information indicating the judgment result and traveling state to the control section 105 in consideration of traveling states such as traveling time, a weather during the traveling, time when traveling is performed, and so on.

Besides, for example, the speed information and turning angle information of the present embodiment correspond to heartbeat variation information and driving information of the present invention.

The driver information detecting section 104 detects a heartbeat signal of a driver who drives a vehicle such as the above vehicle and variations in heartbeat of electrocardiogram waveform data and so on. Based on the heartbeat signal and electrocardiogram waveform data, the driver information detecting section 104 acquires driver information (e.g., corresponding to heartbeat variation information and driving information of the present invention) indicating states of the driver that includes a heart rate, heartbeat fluctuations, and so on and outputs the acquired driver information to the control section 105.

For example, the driver information detecting section 104 comprises a detecting part on a part of the steering wheel to detect a heartbeat signal of the driver. By holding the detecting part with both hands, a heartbeat signal, that is, a change in action potential of a heart in a human body on a time base is detected, electrocardiogram waveform data is generated based on the change in action potential of the heart, pieces of information including data of a heart rate (hereinafter, referred to as heart rate data (e.g., corresponding to heart rate data of the present invention)) and data of heartbeat fluctuations (hereinafter, referred to as heartbeat fluctuation data (e.g., corresponding to heartbeat fluctuation data of the present invention)) are outputted to the driver control section 105 based on the electrocardiogram waveform data.

Besides, the heartbeat fluctuations indicate heartbeat variations. Of fluctuations in cardiac cycle, the heartbeat variations are changes in cardiac cycle, the changes being caused by fluctuations in input of an autonomic nerve to a sinus node. When heartbeat variations are analyzed, a peak interval is generally measured for each period of the electrocardiogram waveform data, that is, for each heartbeat.

To be specific, when a heart rate is calculated, the driver information detecting section 104 of the present embodiment generates electrocardiogram waveform data from an obtained heartbeat signal, calculates R wave, which indicates a maximum value of each period of the electrocardiogram waveform data, and a value indicating an interval of the R wave (hereinafter, referred to as peak waveform data), takes the reciprocal of an inputted peak interval value for the R wave and the interval of the R wave, multiplies the reciprocal by 60 to calculate a heart rate of one minute, and outputs the calculated heart rate data to the control section 105.

Further, when heartbeat fluctuations are calculated, the driver information detecting section 104 generates electrocardiogram waveform data from an obtained heartbeat signal as in the case of the calculation of a heart rate, calculates R wave, which indicates a maximum value of each period of the electrocardiogram waveform data, and a value indicating an interval of the R wave, successively analyzes changes in frequency and amplitude of components of heartbeat variations as functions of time by using CDM (Complex Demodulation), and calculates heartbeat fluctuation data.

Additionally, according to CDM, calculated R-R interval data is multiplied by a predetermined frequency of a sinusoidal wave (e.g., 0.3 Hz) with a modulator, an orthogonal intermediate frequency component I (in Phase) and a Q (quadrature) signal are generated, demodulation is performed from the I and Q signals by a low-pass filter having a predetermined bandwidth (e.g., 0.15 Hz), and heartbeat fluctuations are calculated.

Analysis data of music data that is analyzed by the data analyzing section 102, traveling information of the vehicle that is detected by the traveling state detecting section 103, and driver information detected by the driver information detecting section 104 are inputted to the control section 105. The control section 105 judges mental and physical states of the driver based on the inputted analysis information, traveling information, and driver information, and controls selection of music data to be reproduced (hereinafter, referred to as a reproduction controlling operation).

To be specific, as described above, heart rate data and heartbeat fluctuation data are inputted to the control section 105 as driver information. When the mental and physical states of the driver are judged based on the heart rate data and heartbeat fluctuation data of the driver, a threshold value of heart rate and heartbeat fluctuation is determined based on inputted traveling information.

Further, the control section 105 judges a state of the driver based on the threshold values of the heart rate and heartbeat fluctuation data determined thus, and instructs the reproducing section 106 to stop or suspend reproduction of music data having elements of music components that brings in or enhances the mental and physical states in such a manner as to maintain or develop the states.

Namely, based on the threshold values of the heart rate and the heartbeat fluctuation, the control section 105 judges mental and physical states, to be specific, judges whether sleepiness, tension, or fatigue is present. The control section 105 instructs the reproducing section 106 to suspend or stop the reproduction of music data having music components that brings in or enhances sleepiness when the driver becomes sleepy, to suspend or stop the reproduction of music data having elements that brings in or enhances tension when the driver becomes tensed, or to suspend or stop the reproduction of music data having elements that brings in or enhances fatigue when the driver becomes fatigued.

Based on traveling information indicating inputted traveling states such as a kind of traveling road where a vehicle travels, a traveling state of the vehicle, traveling time, a weather at the traveling, and time elapsed from the start of the traveling, the control section 105 determines threshold values of a heart rate and heartbeat fluctuations that are used for judging mental and physical states.

For example, in the case where a vehicle normally travels on an ordinary road, when a heart rate is less than a threshold level "65", it is judged that "sleepiness" is present. And when a heartbeat fluctuation is more than a threshold level "20 msec", it is judged that "sleepiness" is present. When a heart rate is more than a threshold level "90", it is judged that "tension" is present. And when a heartbeat fluctuation is less than a threshold level "5 msec", it is judged that "tension" is present. In the case where a vehicle normally travels on an ordinary road, when a heart rate is less than a threshold level "70" it is judged that "fatigue" is present. And when a heartbeat fluctuation is more than a threshold level "20 msec" it is judged that "sleepiness" is present. Further, when a vehicle travels on an expressway at high speed, thresholds of a heart rate and heartbeat fluctuations are reduced.

Moreover, based on inputted analysis data, the control section 105 judges whether the reproduction of music data to be reproduced is suspended or not or whether the reproduction of music data being currently reproduced is stopped or not. The control section 105 instructs the reproducing section 106 to suspend or stop the reproduction of music data, selects another piece of music data from the database 101, and instructs the reproducing section 106 to reproduce the selected piece of music data.

For example, as described above, when it is judged that "sleepiness" is present in a state of the driver, the control section 105 refers to the analysis data of music data to be reproduced or being reproduced music data. When a tempo of the music data is 70 BPM (Beat Per Minute) or less, the control section 105 provides instructions to suspend or stop the reproduction of the music data.

Moreover, as described above, when it is judged that "tension" is present in the state of the driver, the control section 105 refers to the analysis data of music data to be reproduced or being reproduced music data. When a tempo of the music data is 90 BPM (Beat Per Minute) or more, the control section 105 provides instructions to suspend or stop the reproduction of the music data.

Furthermore, when it is judged that "fatigue" is present in the state of the driver, the control section 105 refers to the analysis data of music data to be reproduced or being reproduced music data. When a tempo of the music data is 90 BPM (Beat Per Minute) or more, an acoustic image is close, or a difference in sound pressure between the right and left is 10 dB or more, the control section 105 provides instructions to suspend or stop the reproduction of the music data.

When the control section 105 refers to analysis data in each of the states to find a tempo and so on are different from those mentioned above, reproduction is started or continued.

Further, when a state of the driver is judged, in the case where corresponding music data is not available in the database 101, the control section 105 notifies the driver of "no corresponding music data" on a display part and the like (not shown).

In response to the instruction of the control section 105, the reproducing section 106 reproduces a piece of music data from a plurality of pieces of music data stored in the database 101. When it is judged that the music data to be reproduced or the music data being reproduced has components that brings in or enhances the mental and physical states of the driver in the above manner, the reproducing section 106 stops or suspends the reproduction of the music data.

Figure 2:
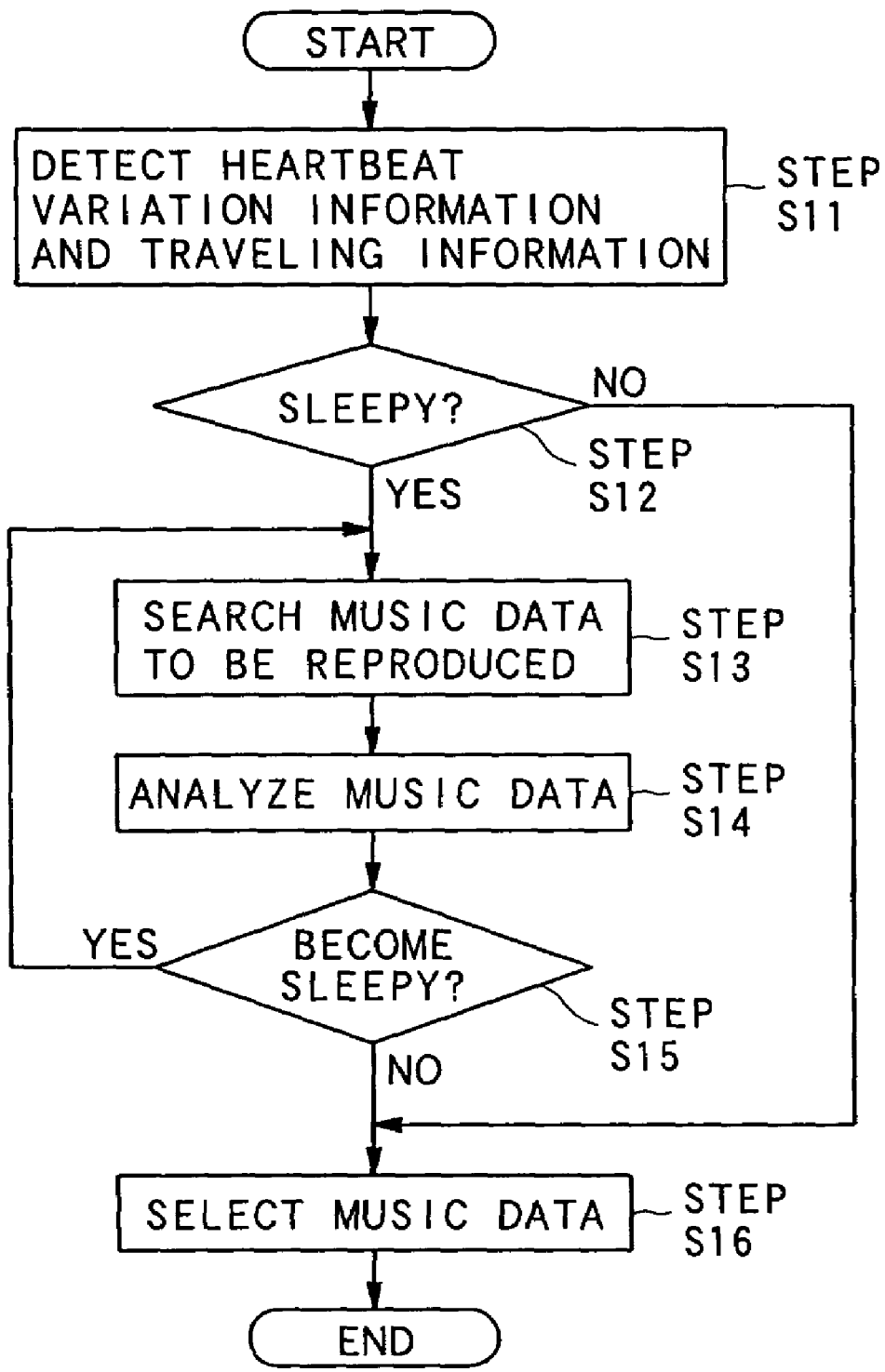
FIG. 2 is a flowchart showing a reproduction controlling operation when the mental and physical states of a driver are judged to be "sleepiness" in Embodiment 1.
Figure 3:
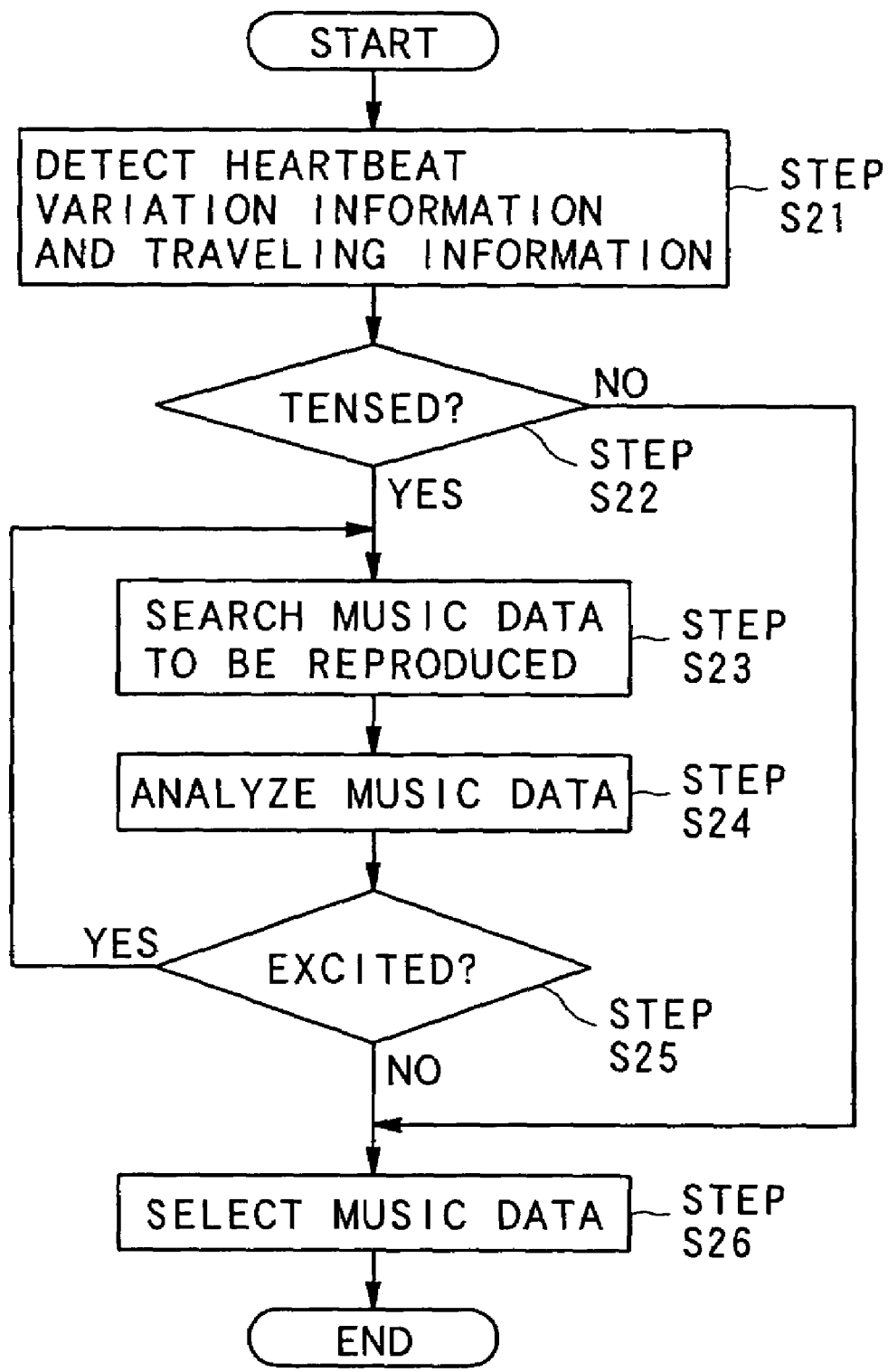
FIG. 3 is a flowchart showing a reproduction controlling operation when the mental and physical states of the driver are judged to be "tension" in Embodiment 1.
Figure 4:
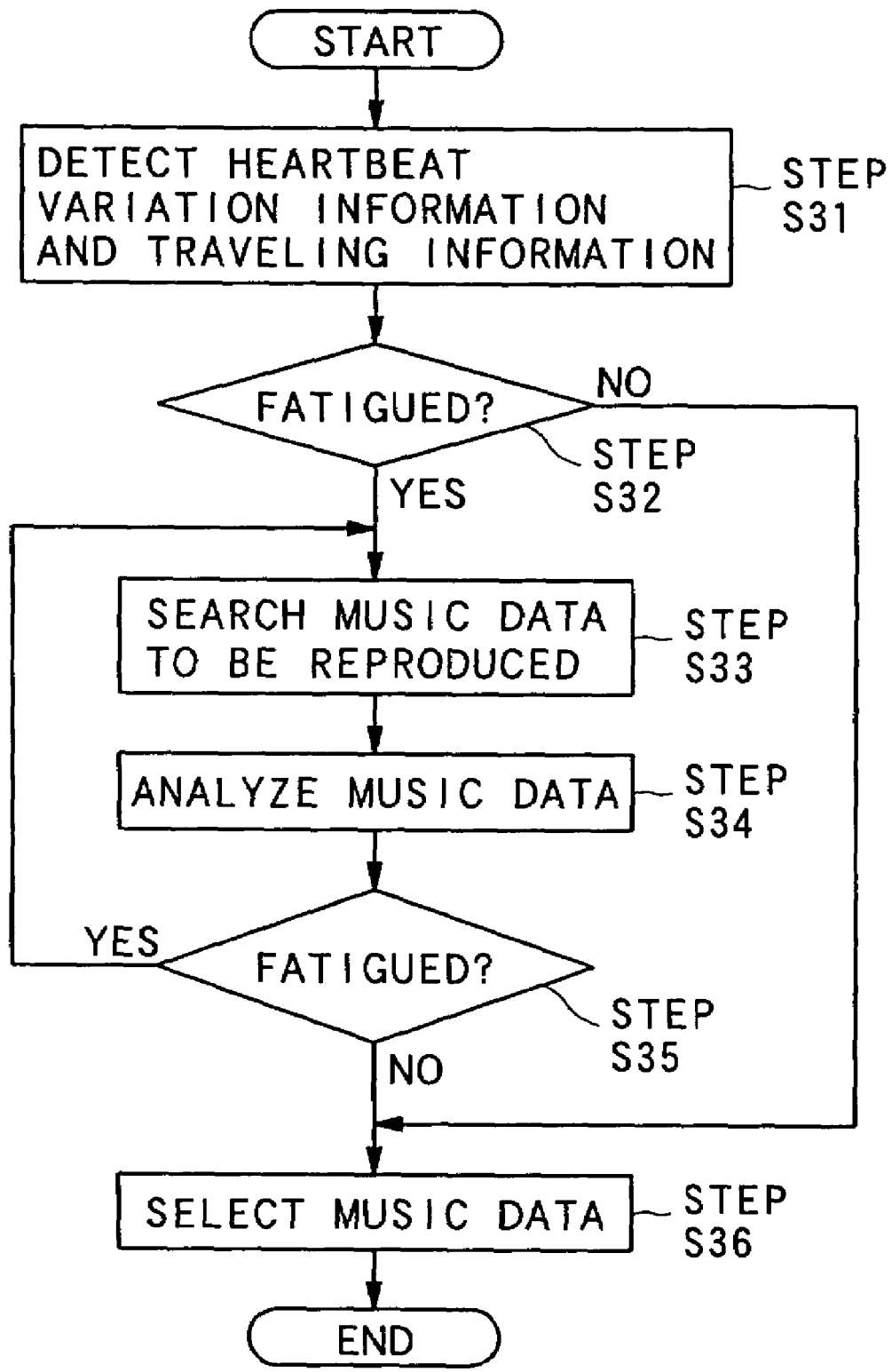
FIG. 4 is a flowchart showing a reproduction controlling operation when the mental and physical states of the driver are judged to be "fatigue" in Embodiment 1.

Referring to FIGS. 2 to 4, the following will discuss a reproduction controlling operation which is performed at the start of reproduction or during reproduction of music data.

Additionally, the reproduction controlling operation described below is started when the user provides instructions to reproduce music data stored in the database 101, by using an operating part and the like (not shown), and the operation is continued during the reproduction of the music data. For example, the reproduction controlling operation is repeated every ten seconds.

Further, reproduction controlling operations described below are performed in parallel.

First, the following will discuss a reproduction controlling operation when the control device judges that the mental and physical states of the driver have "sleepiness".

Additionally, FIG. 2 is a flowchart showing the reproduction controlling operation when it is judged that the mental and physical conditions of the driver have "sleepiness".

First, when the driver or another user of the vehicle provides instructions to start the reproduction of music data stored in the database 101, the control section 105 controls the driver information detecting section 104 and the traveling state detecting section 103 to detect heartbeat variations such as a heart rate and heartbeat fluctuations of the driver and a traveling state of the vehicle, and the control section 105 acquires heartbeat variation information such as heart rate information or heartbeat fluctuation information and traveling information such as speed information or turning angle information (step S11).

Besides, when reproduction of music data has been already started, regardless of the starting instructions, the control section 105 causes the detecting sections to detect heartbeat variations such as a heart rate and heartbeat fluctuations of the driver and a traveling state of the vehicle after predetermined time elapses since the operation is previously performed, and the control section 105 acquires the heartbeat variation information and traveling information.

Further, in this operation, the control section normally provides instructions to reproduce a plurality of pieces of music data in the manners of random playing for optionally reproducing music data, program playing for reproducing pieces of music data in an order predetermined by the user, or album playing for reproducing a plurality of pieces of music data having commonality, for example, an album of an artist.

Next, based on the acquired heartbeat variation information and traveling information, the control section 105 judges whether or not the driver is in mental and physical states of sleepiness (step S12). When the control section 105 judges that the driver is not in mental and physical states of sleepiness, a shift is made to step S16, and the control section 105 selects music data indicated by the user and causes the reproducing section to reproduce the music data as will be described later.

As described above, the control section 105 sets threshold values based on the traveling information and judges whether the heartbeat information is equal to or larger than the threshold values or equal to or smaller than the threshold values.

Meanwhile, when the control section 105 judges that the driver is in mental and physical states of sleepiness, the following operations are performed.

First, the control section 105 searches the database 101 and retrieves music data indicated by the user (step S13).

As will be described later, when a return is made from step S15, the control section 105 retrieves music data indicated by the user as a reproduction candidate next to the music data indicated by the user.

Moreover, when there is no available music data to be reproduced, the control section suspends the operation at this point and causes the operating part to display the suspension.

Subsequently, the control section 105 outputs the music data indicated by the user to the data analyzing section 102 and controls the data analyzing section 102 to analyze audio components of the music data (step S14).

To be specific, the data analyzing section 102 analyzes a tempo, a beat, a rhythm pattern, and music components of a specific chord of music data and outputs the analyzed music components as music component information to the control section 105.

When reproduction of music data has been already started by the reproducing section 106, the data analyzing section 102 stores music components of analyzed music data in an internal memory and so on and outputs the components.

Subsequently, regarding the mental and physical states in which the driver becomes sleepy, the control section 105 judges whether or not inputted music component information has components that brings in or enhances the mental and physical states of sleepiness, that is, whether or not the driver becomes sleepy when listening to the music data (step S15). When the control section 105 judges that the driver becomes sleepy when listening to the music data, a return is made to step S13.

Meanwhile, when the control section 105 judges that the driver does not become sleepy even when listening to the music data, the control section 105 selects reproduction of music data indicated by the user and controls the reproducing section 106 to start reproduction of the music data (step S16).

When the reproduction of music data has been already started by the reproducing section 106, the control section 105 controls the reproducing section 106 so as to keep reproducing the music data and completes the operation.

Next, the following will discuss a reproduction controlling operation when the control device judges that the mental and physical states of the driver have "tension".

Besides, FIG. 3 is a flowchart showing the reproduction controlling operation when it is judged that the mental and physical conditions of the states of the driver are of "tension".

When the driver or another user of the vehicle provides instructions to start the reproduction of music data stored in the database 101, the control section 105 controls the driver information detecting section 104 and the traveling state detecting section 103 to detect heartbeat variations such as a heart rate and heartbeat fluctuations of the driver and a traveling state of the vehicle, and the control section 105 acquires the heartbeat variation information and traveling information (step S21).

As in the case of the reproduction controlling operation for "sleepiness", when reproduction of music data has been already started, regardless of the starting instructions, the control section 105 causes the detecting sections to detect heartbeat variations such as a heart rate and heartbeat fluctuations of the driver and a traveling state of the vehicle after predetermined time elapses since the operation is previously performed, and the control section 105 acquires the heartbeat variation information and traveling information.

Further, in this operation, the control section normally provides instructions to reproduce a plurality of pieces of music data in the manners of random playing for optionally reproducing music data, program playing for reproducing pieces of music data in an order predetermined by the user, or album playing for reproducing a plurality of pieces of music data having commonality, for example, an album of an artist.

Next, based on the acquired heartbeat variation information and traveling information, the control section 105 judges whether or not the driver is in mental and physical states of tension (step S22). When the control section 105 judges that the driver is in mental and physical states not of tension, a shift is made to step S26, and the control section 105 selects music data indicated by the user and causes the reproducing section to reproduce the music data as will be described later.

As described above, the control section 105 sets threshold values based on the traveling information and judges whether the heartbeat variation information is equal to or larger than the threshold values or equal to or smaller than the threshold values as follows: for example, when heartbeat variation information is heart rate data, it is judged whether or not the heart rate data is equal to or larger than the set threshold values, and when the heartbeat variation information is heartbeat fluctuation data, it is judged whether or not the heartbeat fluctuation data is equal to or smaller than the set threshold values.

Meanwhile, when the control section 105 judges that the driver is in mental and physical states of tension, the following operations are performed.

First, the control section 105 searches the database 101 and retrieves music data indicated by the user (step S23).

As will be described later, when a return is made from step S25, the control section 105 retrieves music data indicated by the user as a reproduction candidate next to the music data indicated by the user.

Moreover, when there is no available data to be reproduced, the control section suspends the operation at this point and causes the operating part (not shown) to display the suspension.

Subsequently, the control section 105 outputs the music data indicated by the user to the data analyzing section 102 and controls the data analyzing section 102 to analyze audio components of the music data (step S24).

To be specific, the data analyzing section 102 analyzes a tempo, a beat, a rhythm pattern, and music components of a specific chord of music data and outputs the analyzed music components as music component information to the control section 105.

When reproduction of music data has been already started by the reproducing section 106, the data analyzing section 102 stores the music components of analyzed music data in the internal memory and so on and outputs the components.

Subsequently, regarding the mental and physical states in which the driver is tensed, the control section 105 judges whether or not inputted music component information has components that brings in or enhances the mental and physical states of tension, that is, whether or not the driver is tensed when listening to the music data (step S25). When the control section 105 judges that the driver is tensed by listening to the music data, a return is made to step S23.

Meanwhile, when the control section 105 judges that the driver is not tensed by listening to the music data, the control section 105 selects reproduction of music data indicated by the user and controls the reproducing section 106 to start reproduction of the music data (step S26).

When the reproduction of music data has been already started by the reproducing section 106, the control section 105 controls the reproducing section 106 so as to keep reproducing the music data and completes the operation.

Next, the following will discuss a reproduction controlling operation when the control device judges that the mental and physical states of the driver are of "fatigue".

Besides, FIG. 4 is a flowchart showing the reproduction controlling operation when it is judged that the mental and physical conditions of "fatigue".

First, when the driver or another user of the vehicle provides instructions to start the reproduction of music data stored in the database 101, the control section 105 controls the driver information detecting section 104 and the traveling state detecting section 103 to detect heartbeat variations such as a heart rate and heartbeat fluctuations of the driver and a traveling state of the vehicle, and the control section 105 acquires the heartbeat variation information and traveling information (step S31).

As in the case of the reproduction controlling operation for "sleepiness", when reproduction of music data has been already started, regardless of the starting instructions, the control section 105 causes the detecting sections to detect heartbeat variations such as a heart rate and heartbeat fluctuations of the driver and a traveling state of the vehicle after predetermined time elapses since the operation is previously performed, and the control section 105 acquires the heartbeat variation information and traveling information.

Further, in this operation, the control section normally provides instructions to reproduce a plurality of pieces of music data in the manners of random playing for optionally reproducing music data, program playing for reproducing pieces of music data in an order predetermined by the user, or album playing for reproducing a plurality of pieces of music data having commonality, for example, an album of an artist.

Next, based on the acquired heartbeat variation information and traveling information, the control section 105 judges whether or not the driver is in mental and physical states of fatigue (step S32). When the control section 105 judges that the driver is not in mental and physical states of fatigue, a shift is made to step S36, and the control section 105 selects music data indicated by the user and causes the reproducing section to reproduce the music data as will be described later.

As described above, the control section 105 sets threshold values based on the traveling information and judges whether the heartbeat information is equal to or larger than the threshold values or equal to or smaller than the threshold values as follows: for example, when heartbeat variation information is heart rate data, it is judged whether or not the heart rate data is equal to or smaller than the set threshold values, and when the heartbeat variation information is heartbeat fluctuation data, it is judged whether or not the heartbeat fluctuation data is equal to or larger than the set threshold values.

Meanwhile, when the control section 105 judges that the driver is in mental and physical states of fatigue, the following operations are performed.

First, the control section 105 searches the database 101 and retrieves music data indicated by the user (step S33).

Besides, as will be described later, when a return is made from step S35, the control section 105 retrieves music data indicated by the user as a reproduction candidate next to the music data indicated by the user.

Moreover, when there is no available music data to be reproduced, the control section suspends the operation at this point and causes the operating part (not shown) to display the suspension.

Subsequently, the control section 105 outputs the music data indicated by the user to the data analyzing section 102 and controls the data analyzing section 102 to analyze audio components of the music data (step S34).

To be specific, the data analyzing section 102 analyzes a tempo, a beat, a rhythm pattern, a difference in outputted sound pressure between the right and left, and sound image localization and outputs the analyzed music components as music component information to the control section 105.

When reproduction of music data has been already started by the reproducing section 106, the data analyzing section 102 stores the music components of analyzed music data in the internal memory and so on and outputs the components.

Subsequently, regarding the mental and physical states in which the driver is fatigued, the control section 105 judges whether or not inputted music component information has components that brings in or enhances the mental and physical states of the fatigue, that is, whether or not the driver is fatigued when listening to the music data (step S35).

When the control section 105 judges that the driver is fatigued by listening to the music data, a return is made to step S33.

Meanwhile, when the control section 105 judges that the driver is not fatigued by listening to the music data, the control section 105 selects reproduction of music data indicated by the user and controls the reproducing section 106 to start reproduction of the music data (step S36).

When reproduction of music data has been already started by the reproducing section 106, the control section 105 controls the reproducing section 106 so as to keep reproducing the music data and completes the operation.

As described above, the present embodiment comprises a driver information detecting section 104 for acquiring driving information which includes heartbeat variation information indicating heartbeat variations such as a heart rate and heartbeat fluctuations of the driver who drives the vehicle, the data analyzing section 102 which analyzes music components included in music data and acquires music component information indicating audio components of the analyzed music data, and the control section 105 which judges the mental and physical states of the driver based on the acquired driver information, selects music data to be reproduced based on music component information relative to the judged mental and physical states of a driver, and controls the reproducing section 106 to reproduce the selected music data.

Therefore, when instructions are provided to reproduce music data, for example, even in the case where the driver is in mental and physical states of sleepiness, tension, and fatigue, it is possible to stop or suspend the reproduction of music that brings in or enhances the mental and physical states and to reproduce music data indicated by the user such as a driver. Consequently, it is possible to reproduce music matching the taste of the user such as a driver while maintaining awakening of the driver of a mobile unit.

Further, according to the present embodiment, when the reproducing section 106 starts reproducing music data or performs reproduction, in the case where the control section 105 judges that the driver is in the predetermined mental and physical states of sleepiness, tension, or fatigue, the control section 105 judges whether or not components that brings in or enhances the judged mental and physical states are present based on the audio component information relative to the judged mental and physical states of music data, which indicates sound data provided when reproduction is started or reproduction is performed. When the control section 105 judges that the audio components of the music data have components that brings in or enhances the mental and physical states, the control section 105 selects music data different from the music data as music data to be reproduced by the reproducing section 106, and controls the reproducing section 106 to reproduce the selected music data.

Therefore, in the case where instructions are provided to reproduce music data, for example, even when the driver is in mental and physical states of sleepiness, tension, and fatigue, it is possible to stop or suspend the reproduction of the music that brings in or enhances the mental and physical states and to reproduce music data which is different from the stopped or suspended music data and is indicated by the user such as a driver. Hence, it is possible to reproduce music matching the taste of the user while maintaining awakening of the driver of the mobile unit.

Moreover, according to the present embodiment, the control section 105 judges at least one of the mental and physical states of fatigue, sleepiness, and tension of the driver based on heartbeat variation information acquired by the driver information detecting section 104.

Therefore, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

Moreover, according to the present embodiment, the control section 105 acquires traveling information, which is detected by the traveling information detecting section 103 and indicates a traveling state of a mobile unit, together with heartbeat variation information detected by the driver information detecting section 104.

Therefore, since the mental and physical states of the driver can be judged in view of the traveling state, the mental and physical states of the driver can be judged in an appropriate manner.

Additionally, according to the present embodiment, in the above reproduction controlling operations, music data to be reproduced is analyzed after the mental and physical states of the driver are detected. The analysis may be performed in advance by the data analyzing section 102 before each of the reproduction controlling operations is performed.

Moreover, according to the present embodiment, music data is stored in the database 101 and the music data is reproduced by the reproducing section 106. Sound data such as human voice and natural sound may be stored instead of the music data and the sound data may be reproduced.

Furthermore, according to the present embodiment, the reproduction of music data is controlled by the above reproduction controller. A similar reproduction controlling operation of music data may be performed as follows: a computer and a recording medium are provided in the reproduction controller, a program for performing the reproduction controlling operation of music data is stored in the recording medium, and a selection controlling program for the music data is read by the computer.

Further, in the reproduction controller for executing a reproduction controlling program for movement, a recording medium may be constituted by a recording medium such as a DVD and a CD.

In this case, the data analyzing section 102 comprises a reading device for reading the program from the recording medium.

[Embodiment 2]

Figure 5:
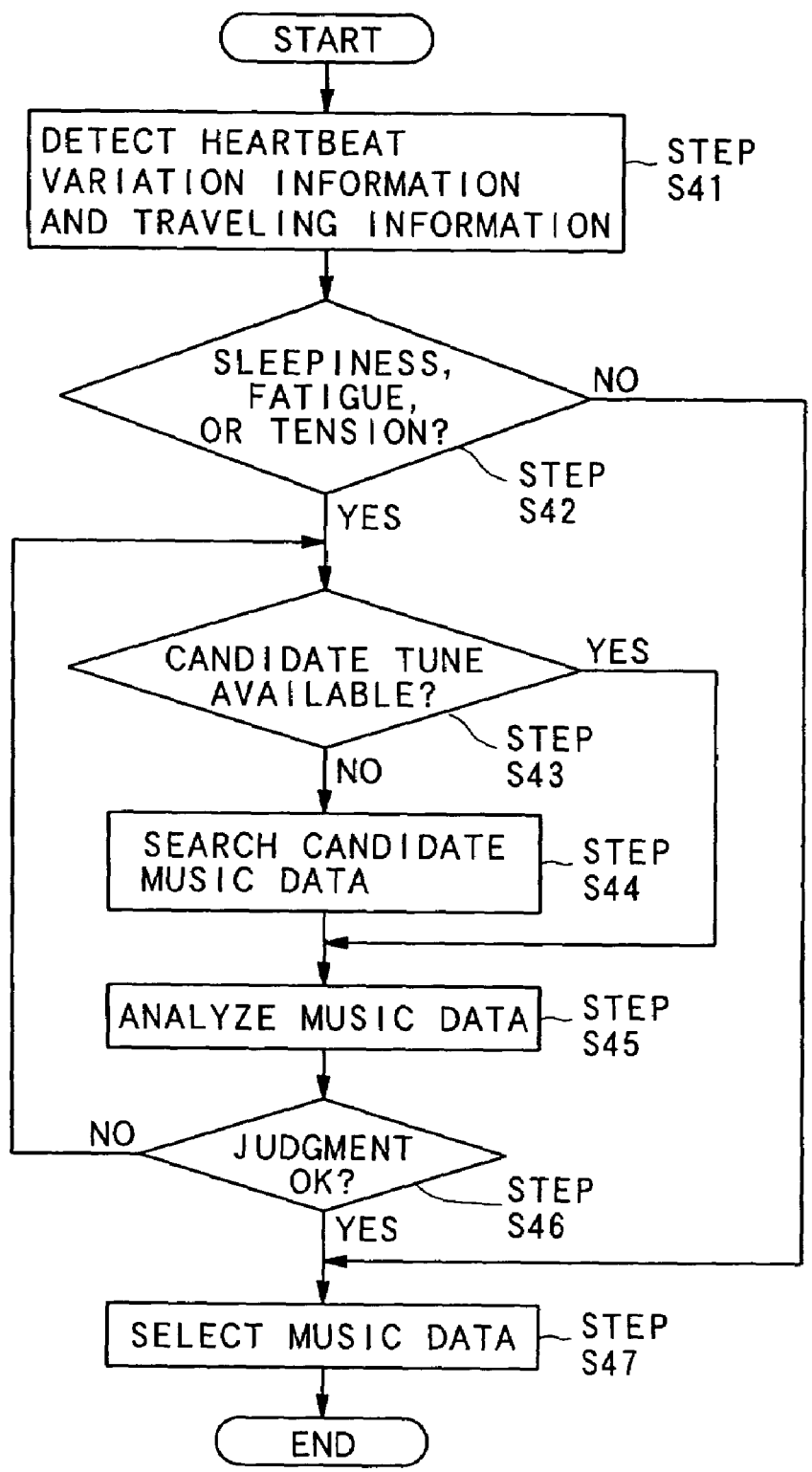
FIG. 5 is a flowchart showing a reproduction controlling operation of music data based on the mental and physical states of the driver according to Embodiment 2 of the present application.
Figure 6:
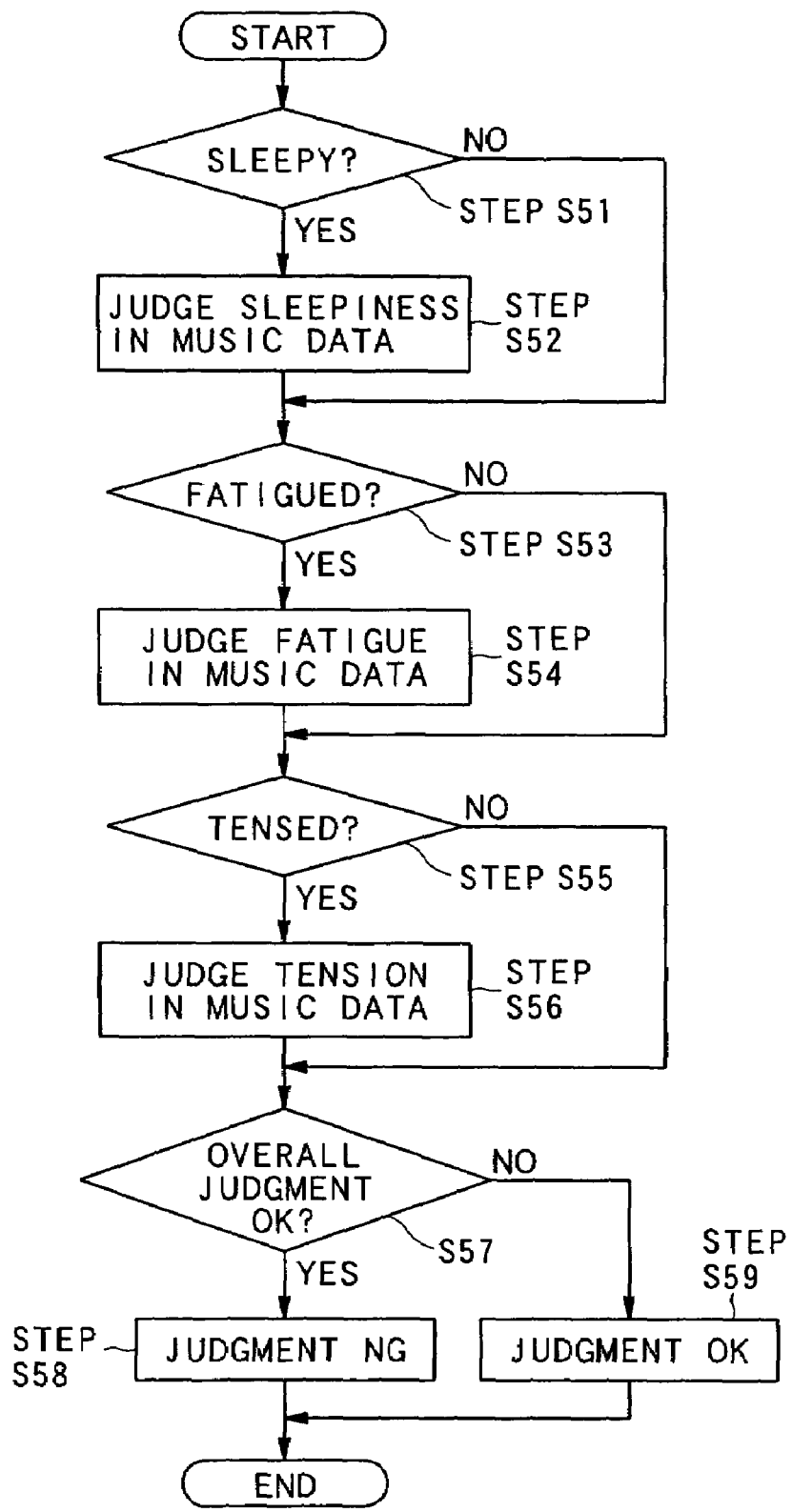
FIG. 6 is a flowchart showing a physical and mental state judging operation which is performed during the reproduction controlling operation of Embodiment 2 and judges mental and physical states of sleepiness, tension, and fatigue.

FIGS. 5 and 6 are diagrams showing Embodiment 2 of a reproduction controller according to the present application.

Unlike Embodiment 1 in which the reproduction controlling operations for mental and physical states of sleepiness, tension, and fatigue are performed in parallel, the present embodiment is characterized in that a single reproduction controlling operation is performed for mental and physical states of sleepiness, tension, and fatigue and the reproduction controlling operation of the present embodiment is characterized in that when the user provides instructions to control reproduction, it is judged whether music data to be reproduced or music data having been reproduced is present or not. The other configurations and the reproduction controlling operations for mental and physical states are the same as those of Embodiment 1. Thus, the same members are indicated by the same reference numerals and the description thereof is omitted.

FIGS. 5 and 6 are flowcharts showing selecting operations in the reproduction controller of the present embodiment.

Referring to FIG. 5, the following will firstly discuss a reproduction controlling operation performed at the start of reproduction of music data or during reproduction of the music data.

FIG. 5 is a flowchart showing the reproduction controlling operation of music data based on the mental and physical states of a driver.

Further, as with Embodiment 1, the reproduction controlling operation described below is started when a reproducing section 106 starts reproducing music data, and the reproduction controlling operation continues until the reproduction of music data is completed. For example, the reproduction controlling operation is repeated every ten seconds.

First, when the driver or another user of a vehicle provides instructions to start reproducing music data stored in a database 101, a control section 105 controls a driver information detecting section 104 and a traveling state detecting section 103 to detect heartbeat variations such as a heart rate and heartbeat fluctuations of the driver and a traveling state of the vehicle, and the control section 105 acquires the heartbeat variation information and traveling information (step S41).

Additionally, when reproduction of music data has been already started, regardless of the starting instructions, the control section 105 causes the detecting sections to detect heartbeat variations such as a heart rate and heartbeat fluctuations of the driver and a traveling state of the vehicle after predetermined time elapses since the operation is previously performed, and the control section 105 acquires the heartbeat variation information and traveling information.

Subsequently, as will be described later, the control section 105 judges whether or not the driver is in mental and physical states of sleepiness, tension, or fatigue in a judging operation of mental and physical states based on the acquired heartbeat variation information and traveling information, that is, whether or not the mental and physical states are "NG" or "OK" (step S43). When the control section 105 judges that the driver is "OK" with mental and physical states not of sleepiness, tension, or fatigue, a shift is made to step S47. As will be described later, the control section 105 selects music data indicated by the user and causes the reproducing section to reproduce the music data.

Additionally, a detailed explanation will be provided later on the operation of judging mental and physical states. In this operation, it is judged whether or not the driver is in mental and physical states of sleepiness, tension, or fatigue based on the acquired heartbeat variation information and traveling information.

Meanwhile, as will be described later, when the control section 105 judges that the driver is "NG" with mental and physical states of sleepiness, tension, and fatigue, it is judged whether or not music data requested by the user for reproduction or music data having been reproduced is present (step S43). When music data requested by the user for reproduction or music data having been reproduced is present, a shift is made to step S45.

Further, when music data requested by the user for reproduction or music data having been reproduced is not present, the following operations are performed.

First, the control section 105 searches the database 101 and retrieves music data serving as a reproduction candidate (step S44).

The reproduction candidate indicates music data of the subsequent tune when the control section 105 provides instructions to reproduce a plurality of pieces of music data in the manners of random playing for optionally reproducing music data, program playing for reproducing pieces of music data in an order predetermined by the user, or album playing for reproducing a plurality of pieces of music data having commonality, for example, an album of an artist.

Moreover, as will be described later, when a return is made from step S46, the control section 105 retrieves music data indicated by the user as a reproduction candidate next to the music data indicated by the user.

Furthermore, when reproducible music data is not available, the control section 105 suspends the operation at this point and causes the operating part to display the suspension.

Subsequently, the control section 105 outputs the music data indicated by the user to a data analyzing section 102 and controls the data analyzing section 102 to analyze audio components of the music data (step S45).

To be specific, the data analyzing section 102 analyzes a tempo, a beat, a rhythm pattern, and music components of a specific chord and outputs the analyzed music components as music component information to the control section 105.

When reproduction of music data has been already started by the reproducing section 106, the data analyzing section 102 stores music components of analyzed music data in an internal memory and so on and outputs the components.

Subsequently, regarding mental and physical states in which the driver is sleepy, tensed, or fatigued, the control section 105 judges whether or not inputted music component information has components that brings in or enhances the mental and physical states of the sleepiness, tension, or fatigue (step S46). When the control section 105 judges that the driver becomes sleepy, tensed, or fatigued when listening to the music data, a return is made to step S43.

To be specific, as will be described later, when it is judged that any one of the mental and physical states of sleepiness, tension, or fatigue is present in the above operation of judging mental and physical states, since the control section 105 has information about the mental and physical states in the internal memory, it is judged whether or not inputted music component information has components that brings in or enhances sleepiness, tension, or fatigue relative to the information of the mental and physical states of sleepiness, tension, or fatigue held by the control section 105.

Meanwhile, when the control section 105 judges that the driver does not get sleepy, tensed, or fatigued by listening to the music data, the control section 105 selects reproduction of music data indicated by the user and controls the reproducing section 106 to start reproducing the music data (step S47).

When reproduction of music data has been already started by the reproducing section 106, the control section 105 controls the reproducing section 106 so as to keep reproducing the music data and completes the operation.

Subsequently, referring to FIG. 6, the following will describe an operation of judging mental and physical states that is performed to judge mental and physical states of sleepiness, tension, and fatigue during the reproduction controlling operation.

Besides, FIG. 6 is a flowchart showing the operation of judging mental and physical states that is performed to judge mental and physical states of sleepiness, tension, and fatigue during the reproduction controlling operation.

First, the control section 105 judges whether or not the driver is in mental and physical states of sleepiness based on acquired heartbeat variation information and traveling information (step S51). When the control section 105 judges that the driver is not in mental and physical states of sleepiness, a shift is made to step S53.

Meanwhile, when the control section 105 judges that the driver is in mental and physical states of sleepiness, the control section 105 stores information of "sleepiness" in the internal memory (step S52) and judges whether or not the driver is in mental and physical states of tension based on the acquired heartbeat variation information and traveling information (step S53).

Subsequently, when the control section 105 judges that the driver is not in mental and physical states of tension, a shift is made to step S55. When the control section 105 judges that the driver is in mental and physical states of tension, the control section 105 stores information of "tension" in the internal memory (step S54).

Next, the control section 105 judges whether or not the driver is in mental and physical states of fatigue based on the acquired heartbeat variation information and traveling information (step S55). When the control section 105 judges that the driver is not in mental and physical states of fatigue, a shift is made to step S57. When the control section 105 judges that the driver is in mental and physical states of fatigue, the control section 105 stores information of "fatigue" in the internal memory.

Then, the control section 105 refers to the internal memory and judges whether or not the above judging operations correspond to at least one of the mental and physical states of sleepiness, fatigue, and tension (hereinafter, referred to as overall judgment (step S56)).

Then, the control section 105 refers to the internal memory. When the internal memory includes information corresponding to any one of the mental and physical states, the control section 105 judges that the mental and physical states are "NG" and completes the operation of judging mental and physical states (step S57). When the internal memory does not include information corresponding to any one of the mental and physical states, the control section 105 judges that the mental and physical states are "OK" and completes the operation of judging the mental and physical states (step S58).

Additionally, in step S57 and step S58, the judgment results are stored in the internal memory of the control section 105. During the reproduction controlling operation, the mental and physical states of the driver are judged by referring to the internal memory.

As described above, the present embodiment comprises a driver information detecting section 104 for acquiring driving information which includes heartbeat variation information indicating heartbeat variations such as a heart rate and heartbeat fluctuations of the driver who drives the vehicle, the data analyzing section 102 which analyzes music components included in music data and acquires music component information indicating audio components of the analyzed music data, and the control section 105 which judges the mental and physical states of the driver based on the acquired driver information, selects music data to be reproduced based on music component information relative to the judged mental and physical states of a driver, and controls the reproducing section 106 to reproduce the selected music data.

Therefore, when instructions are provided to reproduce music data, for example, even in the case where the driver is in mental and physical states of sleepiness, tension, and fatigue, it is possible to stop or suspend the reproduction of music that brings in or enhances the mental and physical states and to reproduce music data indicated by the user such as a driver. Consequently, it is possible to reproduce music matching the taste of the user such as a driver while maintaining awakening of the driver of a mobile unit.

Further, according to the present embodiment, when the reproducing section 106 starts reproducing music data or performs reproduction, in the case where the control section 105 judges that the driver is in the predetermined mental and physical states of sleepiness, tension, or fatigue, the control section 105 judges whether or not components that brings in or enhances the judged mental and physical states are present based on the audio component information relative to the judged mental and physical states of music data, which indicates sound data provided when reproduction is started or reproduction is performed. When the control section 105 judges that the audio components of the music data have components that brings in or enhances the mental and physical states, the control section 105 selects music data different from the music data as music data to be reproduced by the reproducing section 106, and controls the reproducing section 106 to reproduce the selected music data.

Therefore, in the case where instructions are provided to reproduce music data, for example, even when the driver is in mental and physical states of sleepiness, tension, and fatigue, it is possible to stop or suspend the reproduction of the music that brings in or enhances the mental and physical states and to reproduce music data which is different from the stopped or suspended music data and is indicated by the user such as a driver. Hence, it is possible to reproduce music matching the taste of the user while maintaining awakening of the driver of the mobile unit.

Moreover, according to the present embodiment, the control section 105 judges at least one of the mental and physical states of fatigue, sleepiness, and tension of the driver based on heartbeat variation information acquired by the driver information detecting section 104.

Therefore, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

Further, according to the present embodiment, the control section 105 acquires traveling information, which is detected by the traveling information detecting section and indicates a traveling state of the mobile unit, together with heartbeat variation information detected by the driver information detecting section 104.

Therefore, since the mental and physical states of the driver can be judged in view of the traveling state, the mental and physical states of the driver can be judged in an appropriate manner.

According to the present embodiment, in the above reproduction controlling operations, music data to be reproduced is analyzed after the mental and physical states of the driver are detected. The analysis may be performed by the data analyzing section 102 before each of the reproduction controlling operations is performed.

Further, according to the present embodiment, music data is stored in the database 101 and the music data is reproduced by the reproducing section 106. Sound data such as human voice and natural sound may be stored instead of the music data and the sound data may be reproduced.

Furthermore, according to the present embodiment, the reproduction of music data is controlled by the above reproduction controller. A similar reproduction controlling operation of music data may be performed as follows: a computer and a recording medium are provided in the reproduction controller, a program for performing the reproduction controlling operation of music data is stored in the recording medium, and a selection controlling program for the music data is read by the computer.

Further, in the reproduction controller for executing a reproduction controlling program for movement, a recording medium may be constituted by a recording medium such as a DVD and a CD.

In this case, the data analyzing section comprises a reading device for reading the program from the recording medium.

[Embodiment 3]

FIG. 7 is a diagram showing Embodiment 3 of a reproduction controller according to the present application.

Unlike Embodiment 2 in which components such as the traveling information detecting section, the driver information detecting section, the data analyzing section, the control section, and the reproducing section are mounted in a mobile unit such as a vehicle, the present embodiment is characterized in that a traveling information detecting section, a driver information detecting section, and a reproducing section 106 are provided in a terminal mounted in a mobile unit such as a vehicle, a database, a data analyzing section, and a control section are provided on a fixed server device, and transmission and reception are performed between the terminal and the server device via a wireless or wired electric communication line. The other configurations and the reproduction controlling operations of mental and physical states are the same as those of Embodiment 1. Hence, the same members are indicated by the same reference numerals and the description thereof is omitted.

Further, the reproduction controlling operation of the present embodiment is similar to that of Embodiment 1 except that driver information and traveling information that are detected by the traveling information detecting section and the driver information detecting section are transmitted and received and the driver information and the traveling information are inputted to the control section of the server device, and that the presence or absence of reproduction of music data is transmitted to the terminal together with the music data, the presence or absence being judged by the server device. Thus, the explanation of a heart rate measuring operation of the present embodiment is omitted.

FIG. 7 is a structural diagram showing a reproduction controlling system of the present embodiment.

A reproduction controlling system 200 of the present embodiment is constituted by a terminal 210 mounted in a mobile unit such as a vehicle and a server device 220 which is provided on an arbitrary place and is fixed thereon. The terminal 210 and the server device 220 are connected to each other via a wireless or wired electric communication line.

As shown in FIG. 7, the terminal 210 of the present embodiment comprises a traveling state detecting section 103 for detecting a traveling state of a vehicle, a driver information detecting section 104 for detecting a driving state of a driver who drives the vehicle, a transmitting section 211 for transmitting detected traveling information and driver information to the server device 220, a receiving section 212 for receiving a measurement result of a calculated heart rate and reproducible music data, a control section 213 for controlling the sections, and a reproducing section 106 for reproducing received music data.

The transmitting section 211 and the receiving section 212 transmit and receive traveling information, driver information, control data for controlling the sections, and music data to and from the server device 220 via an antenna AT.

Moreover, as shown in FIG. 7, the server device 220 of the present embodiment comprises a receiving section 222 for receiving traveling information and driver information that are transmitted from the terminal 210, a database 101 for storing music data in advance, a data analyzing section 102 for performing data analysis on music data, a transmitting section 221 for transmitting music data and a measurement result of a heart rate to the terminal 210, and a control section 223 which controls selection of music data to be reproduced based on analysis data of analyzed music data, a detected traveling state of a vehicle, and a detected state of the driver and controls each of the sections.

For example, the control section 223 of the present embodiment constitutes, for example, control device of the present invention.

The transmitting section 222 and the receiving section 221 transmit and receive traveling information, driver information, control data for controlling the sections, and music data to and from the server device 220 via the antenna AT.

As described above, the present embodiment comprises a driver information detecting section 104 for acquiring driving information which includes heartbeat variation information indicating heartbeat variations such as a heart rate and heartbeat fluctuations of the driver who drives the vehicle, the data analyzing section 102 which analyzes music components included in music data and acquires music component information indicating audio components of the analyzed music data, and the control section 105 which judges the mental and physical states of the driver based on the acquired driver information, selects music data to be reproduced based on music component information relative to the judged mental and physical states of a driver, and controls the reproducing section 106 to reproduce the selected music data.

Therefore, when instructions are provided to reproduce music data, for example, even in the case where the driver is in mental and physical states of sleepiness, tension, and fatigue, it is possible to stop or suspend the reproduction of music that brings in or enhances the mental and physical states and to reproduce music data indicated by the user such as a driver. Consequently, it is possible to reproduce music matching the taste of the user such as a driver while maintaining awakening of the driver of a mobile unit.

Further, according to the present embodiment, when the reproducing section 106 starts reproducing music data or performs reproduction, in the case where the control section 105 judges that the driver is in the predetermined mental and physical states of sleepiness, tension, or fatigue, the control section 105 judges whether or not components that brings in or enhances the judged mental and physical states are present based on the audio component information relative to the judged mental and physical states of music data, which indicates sound data provided when reproduction is started or reproduction is performed. When the control section 105 judges that the audio components of the music data have components that brings in or enhances the mental and physical states, the control section 105 selects music data different from the music data as music data to be reproduced by the reproducing section 106, and controls the reproducing section 106 to reproduce the selected music data.

Therefore, in the case where instructions are provided to reproduce music data, for example, even when the driver is in mental and physical states of sleepiness, tension, and fatigue, it is possible to stop or suspend the reproduction of the music that brings in or enhances the mental and physical states and to reproduce music data which is different from the stopped or suspended music data and is indicated by the user such as a driver. Hence, it is possible to reproduce music matching the taste of the user while maintaining awakening of the driver of the mobile unit.

Moreover, according to the present embodiment, the control section 105 judges at least one of the mental and physical states of fatigue, sleepiness, and tension of the driver based on heartbeat variation information acquired by the driver information detecting section 104.

Therefore, in the case where instructions are provided to reproduce music data, for example, even when the driver is in the mental and physical states of sleepiness, tension, and fatigue, it is possible to stop or suspend the reproduction of music that brings in or enhances the mental and physical states and to reproduce music data which is different from the stopped or suspended music data and is indicated by the user such as a driver. Hence, it is possible to reproduce music matching the taste of the user such as a driver while maintaining awakening of the driver of the mobile unit.

Further, according to the present embodiment, the control section 105 acquires traveling information, which is detected by the traveling information detecting section and indicates a traveling state of the mobile unit, together with heartbeat variation information detected by the driver information detecting section 104.

Therefore, since the mental and physical states of the driver can be judged in view of the traveling state, the mental and physical states of the driver can be judged in an appropriate manner.

According to the present embodiment, in the above reproduction controlling operations, music data to be reproduced is analyzed after the mental and physical states of the driver are detected. The analysis may be performed by the data analyzing section 102 before each of the reproduction controlling operations is performed.

Like Embodiment 1, the reproduction controlling operations for mental and physical states are performed in parallel in the present embodiment. Like Embodiment 2, a single reproduction controlling operation may be performed for mental and physical states, that is, sleepiness, tension, and fatigue.

Further, according to the present embodiment, music data is stored in the database 101 and the music data is reproduced by the reproducing section 106. Sound data such as human voice and natural sound may be stored instead of the music data and the sound data may be reproduced.

Furthermore, according to the present embodiment, the reproduction of music data is controlled by the above reproduction controller. A similar reproduction controlling operation of music data may be performed as follows: a computer and a recording medium are provided in the reproduction controller, a program for performing the reproduction controlling operation of music data is stored in the recording medium, and a selection controlling program for the music data is read by the computer.

Further, in the reproduction controller for executing a reproduction controlling program for movement, a recording medium may be constituted by a recording medium such as a DVD and a CD.

In this case, the data analyzing section 102 comprises a reading device for reading the program from the recording medium.

Moreover, although the database is provided on the server device in the present embodiment, of course, the database may be provided in the vehicle.

In this case, only control data for controlling reproduction is transmitted and received together with traveling information and driver information between the terminal and the server device.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2002-252643 filed on Aug. 30, 2002 including the specification, claims, drawings and summary is incorporated herein by reference in its entirety.

What is claimed is:

1. A reproduction controlling method for a mobile unit comprising:
   a controlling reproducing process of reproducing a piece of sound data from a plurality of pieces of sound data stored in a database during traveling of the mobile unit,
   a driving information acquiring process of acquiring driving information indicating a driving state of the mobile unit, the driving information including at least heartbeat variation information indicating a variation in heartbeat of a driver who drives the mobile unit,
   a music data acquiring process of acquiring a first music data from a plurality of music data stored in a data base;
   an audio component information acquiring process of analyzing the acquired first music data and acquiring audio component information indicating an audio component of the analyzed first music data,
   a control process of judging mental and physical states of the driver based on the acquired driving information, and selecting whether the acquired first music data is reproduced or not based on the acquired audio component information and the judged mental and physical states of the driver; and
   a reproduction process of reproducing the first music data based on the selection of the control device;
   wherein the reproducing of the first music data is stopped if the first music data has an audio component that maintain or develops the mental and physical states of sleepiness, tension, or fatigue of the driver.

2. The reproduction controlling method for the mobile unit according to claim 1, wherein in the driving information acquiring process, mobile unit information is acquired as the driving information together with the heartbeat variation information, the mobile unit information indicating a traveling state of the mobile unit.

3. The reproduction controlling method for the mobile unit according to claim 1, wherein in the driving information acquiring process, at least one of heart rate data indicating data of a heart rate of the driver and heartbeat fluctuation data indicating data of a fluctuation in heartbeat is acquired as the heartbeat variation information.

4. A reproduction control system for a mobile unit, comprising:
   a database that stores a plurality of pieces of sound data; and
   a control circuit,
   wherein the control circuit reproduces a piece of sound data from the plurality of pieces of sound data while the mobile unit is traveling and acquires driving information indicating a driving state of the mobile unit,
   wherein the driving information includes at least heartbeat variation information indicating a variation in heartbeat of a driver who drives the mobile unit,
   wherein the control circuit analyzes an audio component included in the sound data and acquires audio component information indicating the audio component of the analyzed sound data and that determines mental and physical states of the driver based on the driving information, and
   wherein the control circuit determines whether or not the audio component information has components that bring in or enhance the mental and physical states of the driver and that selects the sound data to be reproduced when the audio component information does not have components that bring in or enhance the mental and physical states of the driver.

5. A reproduction controlling system for a mobile unit, comprising:
   a system controlling reproducing device for reproducing a piece of sound data from a plurality of pieces of sound data stored in a database during traveling of the mobile unit,
   a driving information acquiring device for acquiring driving information indicating a driving state of the mobile unit, the driving information including at least heartbeat variation information indicating a variation in heartbeat of a driver who drives the mobile unit,
   a music data acquiring device for acquiring a first music data from a plurality of music data stored in a data base;
   an audio component information acquiring device for analyzing the acquired first music data and acquiring audio component information indicating an audio component of the analyzed first music data,
   a control device for judging mental and physical states of a driver based on the acquired driving information and selecting whether the acquired first music data is reproduced or not based on the acquired audio component information and the judged mental and physical states of the driver; and
   a reproduction device for reproducing the first music data based on the selection of the control device,
   wherein the control device stops the reproduction of the first music data if the first music data has an audio component that maintains or develops the mental and physical states of sleepiness, tension, or fatigue of the driver.

6. The reproduction controlling system for the mobile unit according to claim 5, wherein the driving information acquiring device acquires traveling information as the driving information together with the heartbeat variation information, the traveling information indicating a traveling state of the mobile unit.

7. The reproduction controlling system for the mobile unit according to claim 6, wherein the driving information acquiring device acquires at least one of a speed of the mobile unit, a traveling road where the mobile unit travels, and a turning angle indicating a direction of the mobile unit relative to a traveling direction of the mobile unit, as mobile unit information.

8. The reproduction controlling system for the mobile unit according to claim 5, wherein the driving information acquiring device acquires at least one of heart rate data indicating data of a heart rate of the driver and heartbeat fluctuation data indicating data of a fluctuation in heartbeat, as the heartbeat variation information.

9. The reproduction controlling system for the mobile unit according to claim 5, wherein the audio component information acquiring device analyzes at least one of sound components of a rhythm pattern, a tempo, a beat, sound image localization, a sound pressure level, and a fundamental note of the sound as sound component information of the sound data, and acquires the analyzed sound component.

10. The reproduction controlling system according to claim 5, wherein the control device selects the first music data so as not to maintain or develop the mental and physical states of sleepiness, tension, or fatigue of the driver.

11. The reproduction controlling system according to claim 5, wherein the control device changes the first music data to a second music data which is selected from the plurality of music data and does not have the audio component that maintains or develops the mental and physical states of sleepiness, tension, or fatigue of the driver.

12. The reproduction controlling system according to claim 11, wherein the control device changes the first music data to the second music data, if the first music data has an audio component that maintains or develops the mental and physical states of sleepiness, tension, or fatigue of the driver.

\* \* \* \* \*